(12) United States Patent
Forstreuter (10) Patent No.: US 10,549,045 B2
(45) Date of Patent: Feb. 4, 2020

(54) DRUG DELIVERY DEVICE FOR DELIVERY OF A MEDICAMENT

(71) Applicant: SANOFI-AVENTIS DEUTSCHLAND GMBH, Frankfurt am Main (DE)

(72) Inventor: Axel Forstreuter, Seeheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1152 days.

(21) Appl. No.: 14/054,913

(22) Filed: Oct. 16, 2013

(65) Prior Publication Data

US 2014/0039412 A1 Feb. 6, 2014

Related U.S. Application Data

(63) Continuation of application No. 12/769,493, filed on Apr. 28, 2010, now Pat. No. 8,585,658.

(30) Foreign Application Priority Data

Apr. 30, 2009 (EP) ..................... 09005996

(51) Int. Cl.
*A61M 5/315* (2006.01)
*A61M 5/24* (2006.01)
*A61M 5/31* (2006.01)

(52) U.S. Cl.
CPC .......... *A61M 5/31515* (2013.01); *A61M 5/24* (2013.01); *A61M 5/3146* (2013.01);
(Continued)

(58) Field of Classification Search
CPC .... A61M 5/31515; A61M 2005/31516; A61M 5/3146; A61M 5/31511–31523;
(Continued)

(56) References Cited

U.S. PATENT DOCUMENTS 533,575 A 2/1895 Wilkens
3,091,240 A * 5/1963 McConnaughey .......................... A61M 5/31596
604/191

(Continued)

FOREIGN PATENT DOCUMENTS

CA 2138528 C 12/1998
CA 2359375 A1 7/2000
(Continued)

OTHER PUBLICATIONS

European Search Report for corresponding EP Application No. 09005996, dated Sep. 15, 2009.
(Continued)

*Primary Examiner* — Bhisma Mehta
*Assistant Examiner* — Laura C Schell
(74) *Attorney, Agent, or Firm* — Fish & Richardson P.C.

(57) ABSTRACT

Various embodiments of drug delivery devices and methods of assembling such devices are provided. In one embodiment, a drug delivery device for dispensing medicament comprises a medicament cartridge, wherein the cartridge comprises (i) a distal end, (ii) a proximal end that is opposite the distal end along a body axis of the cartridge, and (iii) a movable piston arranged substantially at the proximate end of the cartridge. The drug delivery device further comprises a piston rod having a distal end for axially moving the piston in the distal direction during dispensing of a set dose of medicament, wherein a relative axial distance between the distal end of the piston rod and a proximal face of the piston is set during assembly of the drug delivery system. The relative axial position between may be set such that the piston rod and the proximal face of the piston abut each other.

9 Claims, 3 Drawing Sheets

(52) U.S. Cl.
CPC . *A61M 2005/2407* (2013.01); *A61M 2207/00* (2013.01); *Y10T 29/49826* (2015.01)

(58) Field of Classification Search
CPC ............ A61M 31/005; A61M 5/007; A61M 5/14546; A61M 5/1456; A61M 5/14566; A61M 5/14216; A61M 5/1422; A61M 5/31543; A61M 5/2422; A61M 5/281; A61M 5/24–2005/2414
See application file for complete search history.

(56) References Cited

U.S. PATENT DOCUMENTS

| | | | |
|---|---|---|---|
| 3,747,479 A | 7/1973 | Nightingale et al. | |
| 4,333,456 A | 6/1982 | Webb | |
| 4,865,591 A | 9/1989 | Sams | |
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,411,489 A | 5/1995 | Pagay et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,196,999 B1 | 3/2001 | Goethel et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,676,642 B2* | 1/2004 | Beebe ............... | A61M 5/31513 604/228 |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 8,187,233 B2 | 5/2012 | Harms et al. | |
| 2001/0047153 A1* | 11/2001 | Trocki ............... | A61M 5/14546 604/155 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0064041 A1* | 4/2004 | Lazzaro ............. | A61M 5/14546 600/432 |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2005/0154353 A1 | 7/2005 | Alheidt | |
| 2006/0153693 A1 | 7/2006 | Fiechter et al. | |
| 2007/0016143 A1 | 1/2007 | Miller et al. | |
| 2009/0275916 A1 | 11/2009 | Harms et al. | |
| 2011/0046567 A1 | 2/2011 | Radmer et al. | |

FOREIGN PATENT DOCUMENTS

| | | |
|---|---|---|
| EP | 0354368 | 2/1990 |
| EP | 0496141 A1 | 7/1992 |
| EP | 0897729 A2 | 2/1999 |
| EP | 0937471 | 8/1999 |
| EP | 0937476 | 8/1999 |
| EP | 1264611 | 12/2002 |
| EP | 1776975 A2 | 4/2007 |
| EP | 1849490 | 10/2007 |
| EP | 1911479 | 4/2008 |
| JP | S56-150549 | 11/1981 |
| JP | s56150549 * | 11/1981 |
| JP | 2004358047 * | 12/2004 |
| WO | 93/07922 A1 | 4/1993 |
| WO | 93/24160 A1 | 12/1993 |
| WO | 99/38554 | 8/1999 |
| WO | 01/10484 | 2/2001 |
| WO | 02/30495 A2 | 4/2002 |
| WO | 02/092153 A2 | 11/2002 |
| WO | 03/080160 A1 | 10/2003 |
| WO | 2006/074171 | 7/2006 |
| WO | 2006/084876 A1 | 8/2006 |
| WO | 2006/087762 | 8/2006 |
| WO | 2007/130061 | 11/2007 |
| WO | 2008/097979 | 8/2008 |
| WO | 2009/095332 | 8/2009 |

OTHER PUBLICATIONS

"Pen-injectors for medical use—Part 1: Pen-injectors—Requirements and test methods," International Standard, reference number: ISO 11608-1:2000(E), first edition Dec. 15, 2000, 32 pages.

* cited by examiner

DRUG DELIVERY DEVICE FOR DELIVERY OF A MEDICAMENT

CROSS REFERENCE TO RELATED APPLICATIONS

The present application is a divisional of U.S. patent application Ser. No. 12/769,493, filed Apr. 28, 2010, which claims the benefit of European Patent Application No. 09005996.5, filed on Apr. 30, 2009. The entire disclosure contents of these applications are herewith incorporated by reference into the present application.

FIELD OF THE INVENTION

This invention relates to drug delivery devices and methods for assembling such devices that allow users to select single or multiple doses of an injectable medicinal product and to dispense the set dosage of the product. In particular, the present invention relates to such devices, which are handled by the patients themselves.

BACKGROUND

Drug delivery devices for administering single or multiple doses of an injectable medical product are well-known in the art. Generally, such devices have substantially the same purpose as that of an ordinary syringe.

Drug delivery devices of this kind have to meet a number of user-specific requirements. For instance, in the case of those with diabetes, many users will be physically infirm and may also have impaired vision. Therefore, these devices need to be robust in construction, yet easy to use, both in terms of the manipulation of the parts and understanding of its operation by a user. In addition, the dose setting must be easy and unambiguous. Further, where the device is to be disposable rather than reusable, the device should be inexpensive to manufacture and easy to dispose of. In order to meet these requirements, the number of parts and steps required to assemble the device, and the overall number of material types the device is made of should be kept to a minimum.

Typically, the medicinal product to be administered is provided in a cartridge (i.e., a "medicament cartridge") that has a moveable piston (also commonly referred to as a "bung", a "stopper" or a "plunger") mechanically interacting with a piston rod of a drive mechanism of the drug delivery device. By applying thrust to the piston in the distal direction, a certain amount of the medicinal fluid is expelled from the cartridge.

Due to inevitable manufacturing tolerances there may exist axial clearance between a cartridge's piston and the piston rod. Typically, prior to a primary use of the device, a user has to conduct a so-called "priming" of the drug delivery device in order to ensure that the axial clearance is eliminated such that the initial dose set and all subsequent doses set are delivered accurately, and that the amount of the medicinal product is disposed in a predefined way.

Since a self-administering user might be physically infirm, it is desirable to simplify or even to eliminate the need for the user to perform the priming procedure.

Document EP 1 911 479 A1 discloses a dose dispensing device, wherein a piston and a piston rod are electromagnetically or magnetically coupled. However, since the generation of an electromagnetic field requires a supply of electric energy, such a solution is generally not applicable to drug delivery devices of pen-injector type.

Further, document U.S. Pat. No. 6,196,999 B1 discloses a coupling mechanism, wherein a syringe plunger coupling element having the form of a rearwardly extending cylindrical extension is centrally located on a rearward face of a syringe plunger. This coupling element contains an interior T-shaped cavity, wherein the walls of said cavity are knurled to aid the grip of the coupling mechanism. The coupling mechanism is located on the forward end of a plunger drive ram proximate to the syringe plunger and is in the form of two pawls. These pawls are biased away from the plunger drive ram's axis of symmetry by springs. Operation of a motor advances the drive ram forward along its longitudinal axis to move the pawls of the coupling mechanism into engagement with the cylindrical extension of the syringe plunger.

As the advancing pawls initially enter the cavity of the plunger extension, their forward ends are forced toward one another by the walls of the cavity, overcoming the outward bias of the springs. In order to eliminate an initial clearance between the plunger and the drive ram, the pawls have to fully enter the cavity to grip the knurled wall of the cavity. Afterwards, the syringe plunger and drive ram will move in a cooperated motion.

SUMMARY

Disclosed herein are various embodiments of drug delivery devices and methods for assembling such devices that allow users to select single or multiple doses of an injectable medicinal product and to dispense the set dosage of the product without priming the drug delivery device prior to use.

In a first aspect, a drug delivery or injection device for dispensing a dose of a medicinal product is provided. The drug delivery device may comprise a holder for a product-containing cartridge (i.e., a medicament cartridge), wherein the cartridge has an axially movable piston arranged substantially at the proximate end of the cartridge. Herein, a "holder" shall be any structure fulfilling the purpose of holding the medicament cartridge in a fixed position relative to other parts of the drug delivery device, such as the cartridge holder housing or the dose setting mechanism housing. Thus, a holder may prevent the cartridge from moving in an axial direction when an axial force is exerted on the piston via the piston rod. For example, a holder may be a portion of a device housing, a thread being engageable with a thread of the cartridge, clamping means for fixation of the cartridge in the device housing, among other possibilities. The drug delivery device may further comprise a dose setting or drive mechanism. The dose setting or drive mechanism typically contains the mechanical parts that allow the dose of medicament to be set by the user and then activated, for example by a dose button, to delivery the set dose. Additionally, the dose setting or drive mechanism is typically located at the proximal portion of the drug delivery device. Any dose setting mechanism known in the art may be used. Herein, various aspects and embodiments of a drug delivery device are described without reference to a dose setting or drive mechanism, however, it should be understood that some of the components/parts described herein may be incorporated into a dose setting or drive mechanism.

In another aspect, the drug delivery device may comprise a piston rod, which is operably engaged with the piston for displacing the piston in the distal direction, thus allowing a well-defined dose of the medicinal product to be purged or expelled from the cartridge. The distal end of the cartridge may be sealed with a membrane or septum, which may be engaged with a needle, a cannula, an infusion tube or similar fluid delivery devices. The cartridge itself may be designed as a replaceable or disposable ampoule, carpule or syringe.

In another aspect the drug delivery device may comprise one or more adjusting members arranged in an axial direction relative to the piston and/or relative to the piston rod. Herein, "adjusting member", "foot member" and "pressure piece" may be used interchangeably to describe the same component of the drug delivery device. The adjusting member may serve to eliminate axial clearance between the piston and the piston rod that might exist due to manufacturing or assembly tolerances of the various components of the drug delivery device.

In another aspect, a distal portion of the piston rod may include an interlock member adapted to interact with the adjusting member for mutually locking, securing, or fixing the piston rod to the adjusting member such that after assembly the adjusting member abuts the proximal end face of the piston irrespective of the relative starting clearance or gap between the proximal face of the piston and the distal end of the piston rod. As used herein, the term "abut" can mean actual touching of two parts or where there a very small clearance or gap between the two parts. In this way, the interaction of the adjusting member and interlock member effectively provides a method to eliminate unwanted clearance, wherein the piston rod itself may remain relatively stationary within the drug delivery device, e.g., with respect to the cartridge or with respect to a housing component of the drug delivery device.

By arranging the adjusting member axially between the piston and the piston rod, the adjusting member itself may provide a clearance-compensating function, e.g., by an axial movement relative to the piston and/or relative to the piston rod. Such axial movement of the adjusting member is predominately governed by the amount of clearance to be eliminated. As soon as the adjusting member reaches a clearance-eliminating position or configuration, it is typically immobilized by at least the interlock member, thus providing a rigid mechanical coupling that fixes the final desired distance between the proximal face of the piston and the distal end of the piston rod. The adjusting member is in a clearance-eliminating position when it abuts the proximal end face of the piston.

If the piston rod is secured such that the above-mentioned abutment exists, then an axial movement of the piston rod in the distal direction is directly and unalterably transferred to the cartridge's piston via the adjusting member. Such a configuration of the piston, adjusting member, and piston rod may be characterized as a unidirectional coupling in the distal direction. Bi-directional coupling may exist in some embodiments but is not desirable if the drug delivery device is reusable. If the drug delivery device is reusable the adjusting member and interlock member may be configured to allow the piston rod to be moved in the proximal direction while the cartridge's piston remains stationary.

In another aspect, the interlock member may be adapted to provide a retention force being substantially larger than an axially directed force required to displace or to move the adjusting member and/or the piston rod, perhaps in the distal direction. In particular, the retention force to be provided by the interlock member is substantially larger than the sum of static and dynamic friction forces required to axially move the piston inside the cartridge plus a force required to expel the medicinal product from the cartridge and to dispense said product in biological tissue. The interlock member and its interaction with the adjusting member should be such that the relative position of piston and piston rod remains unaffected during and after repeated sequences of dose setting and dose dispensing steps.

In a further aspect, the adjusting member may be attached, perhaps during assembly of the drug delivery device or at a pre-assembly stage, to a proximal end of the piston. The adjusting member may comprise a receptacle to slidably receive a distal portion of the piston rod during assembly of the drug delivery device. Depending on the geometric variations of the various mechanical components of the drug delivery device, a post-assembly relative position of the distal end of the piston rod inside the receptacle of the adjusting member may vary within certain tolerable limits. Irrespective of these variations, the interlock member may be adapted to immobilize and/or to lock in position the distal end of the piston rod with the receptacle of the adjusting member. In this way, a coupling or abutment, rigid in compression, between the piston rod and the piston can be established via the adjusting member, irrespective of the axial distance that initially exists between the piston and the piston rod which may be due to manufacturing and/or assembly tolerances.

In another aspect, a drug delivery device is provided, wherein the drug delivery device contains a cartridge comprising (i) a distal end closed by a membrane or septum, which may be pierceable by a needle cannula and (ii) a proximate end that is closed or sealed by a movable piston, wherein the piston is slidable or movable in the distal direction for delivery or injection of a set dose of medicament contained in the cartridge. The device further comprises a piston rod for moving the piston in the distal direction in order to expel a set dose of liquid medicament from the cartridge, wherein a relative axial position or clearance between the distal end of the piston rod and the proximal end or face of the piston is determined and fixed during assembly or manufacture of the injection device. The relative axial position between the piston rod and the piston may be determined and/or fixed such that the piston rod and the piston abut each other.

In another aspect, the piston rod may comprise a rod member and a foot member located at the distal end of the rod member. The foot member may be a separate part or it may be integral to the rod member and it may be axially adjusted through a ratchet connection, or another type of connection, to the rod member, to allow the piston rod to abut, via the adjusting member, the proximal face of the piston. A relative axial position or distance between the foot member and the piston may be determined during assembly of the drug delivery device. Further, a relative axial position or distance between the foot member and the rod member may be determined during assembly of the drug delivery device. In one instance, the relative axial position between the foot member and the rod member may be determined such that the foot member and the rod member abut each other. In order to connect with the rod member, the foot member may comprise one or more resilient attaching teeth or wings, and the rod member may comprise one or more recesses configured to receive the one or more wings of the foot member.

Another aspect includes a method of assembling a drug delivery device that involves bringing a piston rod into abutment with the proximal face of a piston within a cartridge of medicament. An adjusting or foot member can be used to achieve the abutment. Once a desired relative position of the piston rod and piston is achieved, the adjusting or foot member is secured to the piston rod. The relative axial position or distance between the adjusting or foot member and the piston may be variable during assembly of the injection device and can be adjusted and/or set (locked) to a desired distance. The desired relative position of the piston rod and piston may be such that the piston rod and the piston abut each other.

In another aspect, a drug delivery device may include a piston rod having a rod member and an adjusting member, where the adjusting member is positioned substantially at a distal end of the rod member. The adjusting member can be secured, during assembly of the drug delivery device, to the piston rod via an interlock member of the rod member.

In another aspect, a drug delivery device is provided for dispensing medicament comprising a medicament cartridge having a longitudinal axis along the body of the cartridge, wherein the cartridge comprises a distal end and a proximal end. The cartridge also has a movable piston arranged substantially at the proximal end of the cartridge. Further, the drug delivery system comprises a piston rod for axially moving the piston in the distal direction, wherein the piston rod comprises an axial bore extending from a proximal end of the piston rod to a point substantially at a distal end of the piston rod. An adjusting member is located at least partially between the piston rod and the proximal face of the piston, wherein a relative axial distance between the adjusting member and the piston is set by securing the piston rod to the adjusting member during assembly of the drug delivery device through the use of a locking rod configured for insertion into the bore of the piston rod to fix the piston rod to the adjusting member. Accordingly, it can be said that the adjusting member is configured to effectively eliminate an axial clearance between the piston rod and the proximal face of the piston. After securing the piston rod to the adjusting member, the adjusting member and the piston may abut each other.

The adjusting member may comprise at least one resilient securing element and the piston rod may comprise at least one recess configured to receive the at least one securing element such that the piston rod can be secured to the adjusting member. Alternatively, the piston rod may comprise a radially expandable piece positioned substantially at the distal end of the piston rod and the adjusting member may comprise a receptacle, which may be resilient or at least a sturdy, for receiving at least the radially expandable piece of the piston rod such that the piston rod can be secured to the adjusting member. In either of the above cases, the piston rod can be secured to the adjusting member by inserting the locking rod into the bore of the piston rod thereby causing a press fit between the radially expandable piece or the at least one recess of the piston rod and the receptacle or the at least one securing element of the adjusting member respectively.

When assembling the device, the piston in the cartridge within the cartridge holder can push proximally upon a protruding pressure piece or adjusting member causing it to move proximally as well. After assembly of the cartridge holder, the pressure piece abuts at the proximal face of the piston of the ampoule or cartridge. By inserting and pressing a interlocking rod through a bore inside the longitudinal axis of the piston rod, the pressure piece is locked firmly in the relative position with respect to the piston rod and the relative distance between the piston and the distal end of the piston rod is fixed. The interlocking rod can be inserted through a hole in the dose delivery button or knob during the assembly procedure. In this configuration pressure or force in the axial distal direction can be applied directly to the interlocking rod to adjust and lock the pressure piece in place. Alternatively, the interlocking rod can be inserted into the bore of the piston rod and then the dose delivery button is attached. In this configuration the interlocking rod is moved distally by applying force on the dose button which in turn transmits the force to the interlocking rod causing it to move distally as well, thus adjusting and locking the pressure piece in place. In either configuration, once the pressure piece is secured there may exist a slight pressure between the piston rod and the piston as a result of the locked pressure piece. As such, when the piston rod is moved in the distal direction as a result of the user pushing or activating a dose button to administer a set dose, there is immediate contact with the piston inside the ampoule. The invention can be used on disposable or reusable injection devices. Likewise, it can be used on settable as well as fixed dose injection devices.

In a further aspect, the receptacle of the adjusting member and the distal portion of the piston rod are mutually bonded or welded, e.g., by means of an appropriate adhesive or by means of deposition of energy in a region where the receptacle and piston rod overlap in an axial direction. Energy deposition for the purpose of mutually welding the adjusting member and the piston rod's distal portion can be provided by electromagnetic radiation, e.g., by laser irradiation of the respective portions.

In another aspect, a deformable adhesive may be disposed in the receptacle of the adjusting member. The interlocking of the adjusting member and the piston rod is then achieved in a second step by curing the adhesive. The curing of said adhesive and hence the immobilization and mutual interlocking of adjusting member and piston rod can be supported or triggered by energy deposition, e.g., by means of irradiation with electromagnetic radiation or by application of thermal energy.

Typically, according to this aspect, the receptacle is only partially filled with a plastically deformable adhesive, such that the distal end of the piston rod is at least partially insertable into said receptacle. The cross-sectional area of the piston rod may be substantially smaller than the corresponding cross-sectional area of the receptacle. Upon insertion of the piston rod into the receptacle, a circumferential gap between an inner surface of the receptacle and a outer surface of the piston rod should exist in order to receive at least a portion of the deformable adhesive squeezed during insertion of the piston rod into said receptacle.

In a further aspect, the adjusting member is preassembled to the distal portion of the piston rod using a deformable non-cured adhesive or other type of connection such as a ratchet type connection. This kind of assembly might be advantageous since the adjusting member itself does not have to be mounted and/or attached to the proximal end surface or face of the piston. A desired configuration in which the adjusting member and piston are in abutment may be reached during assembly of the drug delivery device.

If an adhesive is used, the adhesive is not cured and remains deformable until the adjusting member is in its desired position with respect to the piston of the cartridge, therefore, it allows for a clearance-compensating or clearance-eliminating axial motion of adjusting member and/or piston rod. In a typical assembly configuration, it is intended that the piston rod with its pre- and provisionally assembled adjusting member is axially displaced during assembly of the drug delivery device such that the adjusting member abuts the piston in a post-assembly configuration. When said abutment configuration has been reached, the adhesive may be cured, thus immobilizing and rigidly connecting adjusting member and piston rod.

In a further aspect, in a pre-assembly configuration, the adjusting member comprises a first adhesive component in its receptacle and the distal portion of the piston rod comprises a second adhesive component of a two-component adhesive. As soon as the two components are brought into contact, a curing procedure may be triggered, which may lead to a bonded connection of adjusting member and piston rod even without the supply of external energy. However, curing of said two-component adhesive might be supported and accompanied by additional deposition of energy.

The above-mentioned aspects that include a bonded connection between an adjusting member's receptacle and a distal portion of a piston rod may be most applicable with disposable drug delivery devices. For refillable drug delivery devices, wherein a used or empty cartridge might be replaced by a new cartridge, the connection between the piston rod and adjusting member may be configured to be releasable.

In a further aspect, the housing of the drug delivery device may comprise a through opening or at least a transparent window for delivery of an adhesive or for the delivery of energy adapted for curing of adhesive disposed between the receptacle of the adjusting member and the distal end of the piston rod. When the housing comprises a transparent window, the window may be substantially transparent for the electromagnetic radiation to be used. The radiation may be used to cure an adhesive or for directly welding and/or interlocking of piston rod and adjusting member.

Additionally or alternatively, the through opening of the housing may be adapted to provide access to an interlock mechanism by means of an applicable tool to be inserted into said through opening for engagement and actuation of the interlock mechanism.

In other aspects, the interlock member may be a ratchet, a round form, a spiky form, fine gearing (such a lacing cord), or opposite and engaging at an offset. One possible configuration radially clamps the receptacle of the adjusting member and the distal portion of the piston rod. In this configuration, either the receptacle is reducible with respect to its inner diameter or the piston rod is adapted to radially expand. This radial clamping mechanism is adapted to be activated irrespective of the position of piston rod and receptacle. The receptacle may comprise a hollow cylindrical shape and the distal portion of the piston rod may be of corresponding cylindrical shape, respectively. The degree of clamping between piston rod and adjusting member's receptacle should exceed the axial force required to displace the adjusting member and/or the piston in distal direction.

In a further aspect, the distal end of the piston rod comprises at least one radially moveable or radially pivotable jaw adapted to interact with the receptacle, in particular with the inner sidewalls of the receptacle. Furthermore, the jaw has a slanted inner surface, which is adapted to engage with a correspondingly slanted surface of an axially moveable lock rod. Additionally, the piston rod comprises a hollow shaft or bore adapted to slidingly receive the axially moveable lock rod. Due to the corresponding beveled surfaces of lock rod and the at least one distally arranged jaw, an axial movement of said lock rod in the distal direction is at least partially transferred to a radially outwardly directed movement of the jaw, leading to the intended radial clamping of the adjusting member and the jaw and hence to a radial clamping of adjusting member and piston rod. In this aspect, by axially removing the lock rod in the proximal direction, the radial clamping can be reduced or even suspended.

In a further aspect, the piston rod comprises a hollow shaft being adapted for axial insertion and guiding of a lock or interlocking rod. The lock rod is adapted to activate a locked mode and/or for eliminating axial clearance between the receptacle and the cartridge's piston. By means of the lock rod, the adjusting member may be driven and pushed in the distal direction until it moves up against a proximal face of the piston.

In another aspect, the adjusting member may be pre-assembled to the distal portion of the piston rod. During assembly of the drug delivery device, the adjusting member may be axially displaced with respect to the piston rod until it reaches an abutment position with the proximal face of the piston. When this abutment position has been reached, in which axial clearance between piston and adjusting member has been eliminated, the adjusting member is at least locked in position with respect to the piston rod. As a consequence, any subsequent distally directed displacement of the piston rod is then directly and unalterably transferred to the piston.

In still another aspect, the invention provides a method of eliminating clearance during or after assembly of the device, which comprises the steps of axially moving the piston rod relative to an adjusting member and/or axially moving the adjusting member relative to the piston for eliminating axial clearance between the piston and the piston rod. After this first step, the piston and the piston rod are mutually locked in position by an interlock member, which is adapted to interact with the adjusting member.

To summarize, drug delivery devices and methods for assembling such devices are provided for axial clearance elimination between a piston and a piston rod, wherein production and manufacturing-related geometric tolerances of mechanical components can be eliminated and compensated for at the site of assembly, i.e., before the drug delivery device is distributed to end users. The clearance elimination mechanism and method of assembly of the drug delivery device can be kept in a low cost range in a mass production process. Inevitable manufacturing or assembly-related tolerances can be eliminated in a fast, reliable and cost-saving way. Furthermore, general handling of the device and user security can be advantageously enhanced.

It will be apparent to those skilled in the pertinent art that various modifications and variations can be made to the disclosed aspects, and that multiple aspects or features of the aspects may be combined, without departing from the spirit and scope of the invention.

BRIEF DESCRIPTION OF THE FIGURES

Without limitation, the present invention will be explained in greater detail below in connection with exemplary embodiments and with reference to the drawings in which.

DETAILED DESCRIPTION

Figure 1:
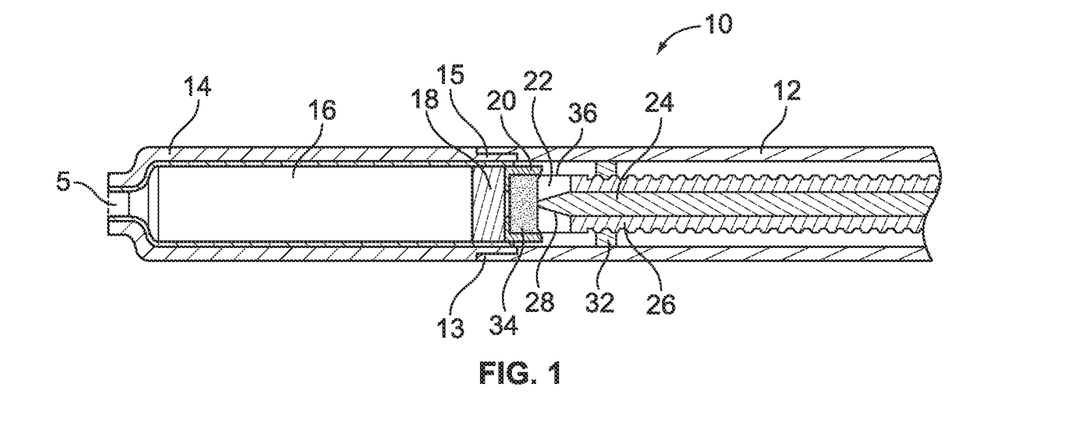
FIG. 1 illustrates a cross-sectional view of a drug delivery device, in accordance with an exemplary embodiment.
Figure 2:
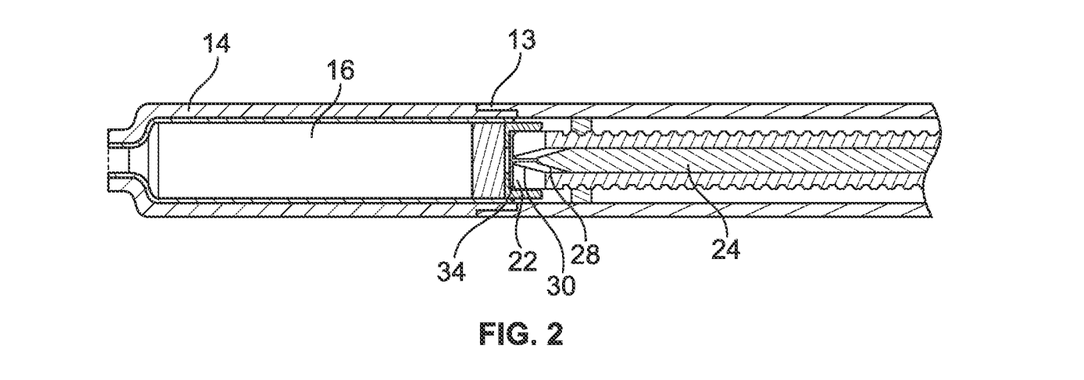
FIG. 2 illustrates the embodiment according to FIG. 1 in a clearance eliminated configuration.
Figure 3:
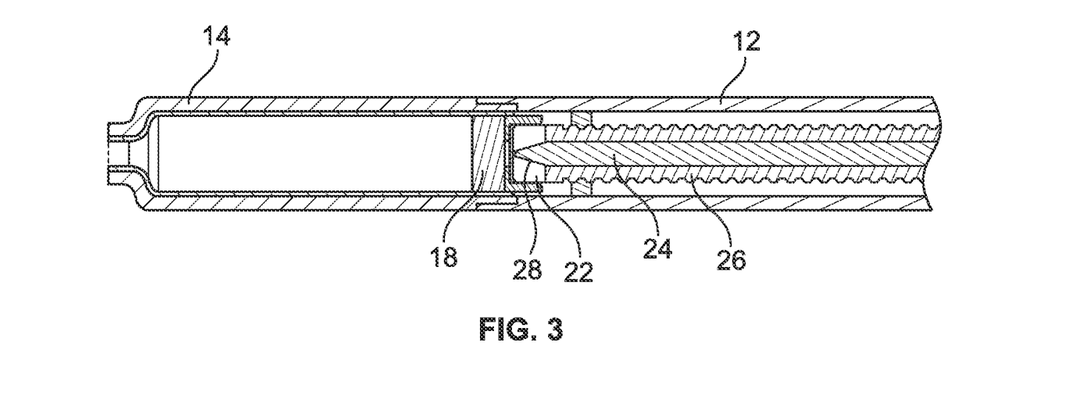
FIG. 3 illustrates the embodiment according to FIGS. 1 and 2 during securement of the piston rod via insertion of the locking rod.

FIGS. 1-3 illustrate one embodiment of a drug delivery device 10 (for simplicity some components have been omitted, such as all the parts of the dose setting mechanism, i.e., a dose button or dose dial sleeve). As shown, the drug delivery device comprises a cartridge 16 filled with a medicinal product (i.e., medicament) to be dose-wise dispensed. The cartridge 16 is mounted in a cartridge holder 14 having a stepped-down neck portion towards its distal end. Herein, "distal" refers to the left side and "proximal" refers to the right side when viewing the figures or put another way, the distal end is the needle end and the proximal end is opposite the distal end and is usually where the dose delivery button or dose dial knob is located. In other embodiments the distal end may be configured differently. For instance, the distal end may be uniform in diameter or tapered.

Fixed to the distal end of the cartridge is a membrane or septum 5 that is configured to be pierceable by a needle cannula (not shown). Near the proximal end of the cartridge 16 is an axially movable piston 18. When subjected to an axial force caused by a distal movement of a piston rod 26, the piston 18 may stepwise move in the distal direction such that an exact and precise amount of the medicinal product is expelled from the cartridge.

The piston rod 26 may be radially secured in the proximal housing component 12 of the drug delivery device 10 in various ways, such as by a mount 32. As shown, the cartridge holder 14 is connected to the housing component 12. According to the embodiment shown in FIGS. 1-3, the cartridge holder 14 and the housing component 12 are arranged in an interleaved manner, wherein a stepped-down neck portion 15 of the cartridge holder 14 is received in a corresponding receptacle portion 13 of the housing component 12. In other embodiments, the distal end of the housing component 12 may by stepped down and the cartridge holder 14 may comprise a corresponding receptacle portion for receiving the stepped-down portion of the housing component 12. In addition, the cartridge holder 14 and the housing component 12 may be connected via threads or another fastening/securing mechanism.

With reference to FIG. 1, there is further illustrated a gap 34 between a distal end of the piston rod and a proximal end face of the piston 18. (Adjusting member 20 hides part of the gap 34.) The axial distance of the gap 34 (i.e., the clearance) may vary due to manufacturing and geometric tolerances of the various components of the drug delivery device 10 and/or varying axial positions of the piston 18 inside the cartridge 16, among other possibilities. In order to eliminate the gap 34, there is provided an adjusting member 20 of hollow-cylindrical shape forming a receptacle for a distal portion of the piston rod 26.

An adjusting member 20 may be pre-assembled to the proximal end face of the piston 18. Alternatively, the adjusting member 20 may be provisionally pre-assembled to the distal portion of the piston rod 26, or in another embodiment the adjusting member 20 may not be pre-assembled at all. In any event, during assembly of the drug delivery device 10, the piston rod 26 may be secured to the adjusting member 20 such that after final assembly of the drug delivery device there is no clearance between the adjusting member 20 and the proximal end face of the piston 18 (i.e., the adjusting member 20 abuts the proximal end face of the piston 18).

As shown in FIGS. 1-3, the piston rod 26 may be secured to the adjusting member 20 by inserting the distal end of the piston rod 26 into the receptacle of the adjusting member 20 and activating or connecting an interlock member 22 of the piston rod 26, which may be achieved with the assistance of a lock rod 24. Although FIGS. 1-3 show the piston rod 26 being inserted and secured to the adjusting member 20 while both components are at least partially within the housing component 12, the piston rod 26 may be inserted and/or secured to the adjusting member 20 while both components are outside the housing component 12.

Figure 6:
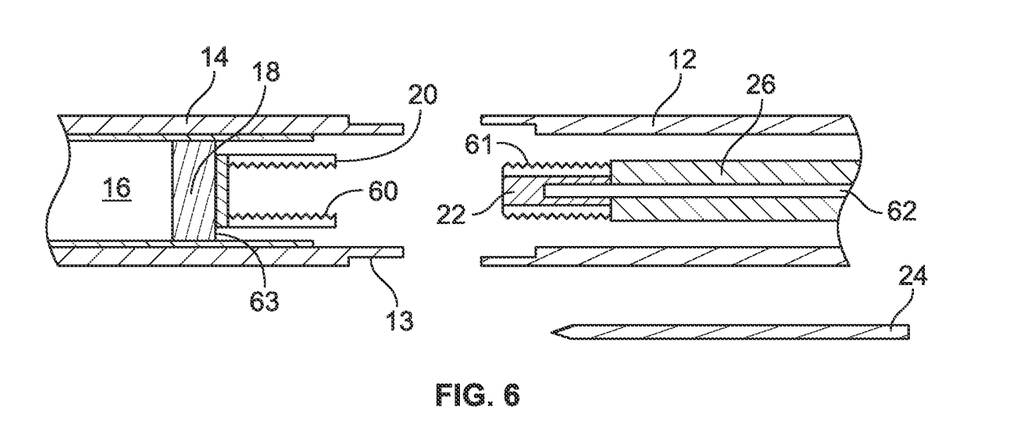
FIG. 6 illustrates a cross-sectional view of a drug delivery device, in accordance with another exemplary embodiment.
Figure 7:
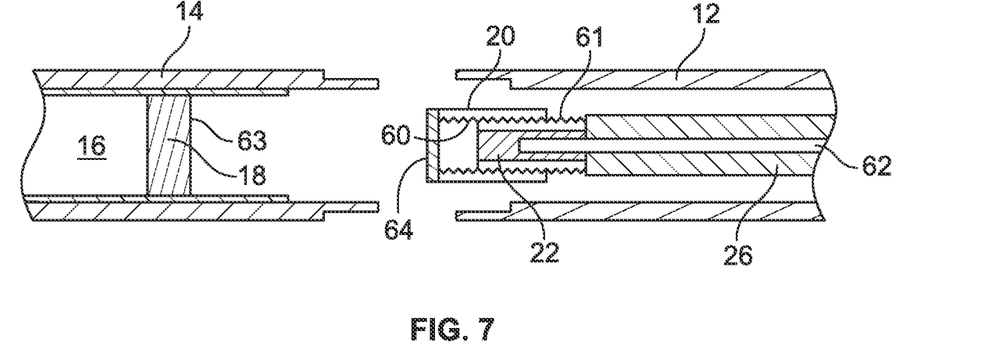
FIG. 7 illustrates a cross-sectional view of a drug delivery device, in accordance with yet another exemplary embodiment.

In the embodiment shown in FIGS. 1-3, when the interlock member 22 is inserted into the receptacle of the adjusting member 20, the interlock member 22 may connect to the adjusting member 20 by a press fit. In other embodiments, the connection may be by any of the following or combination of the following: a ratchet, snap fit, gear teeth, adhesive, press fit, or any known connector. For example, FIGS. 6 and 7 show a ratchet type connection. In accordance with the embodiment shown in FIGS. 1-3, by inserting the lock rod 24 in the distal direction into the hollow bore of the piston rod 26, the beveled surface 28 of interlock member 22 engages the beveled surface 30 of lock rod 24 causing the interlock member 22 to move radially outward, thus generating a press fit with the adjusting member's receptacle.

As shown in FIG. 3, after securing the piston rod 26 to the adjusting member 20, the adjusting member 20 abuts the proximal end face of the piston 18. However, there still exists a small axial clearance between the adjusting member 20 and the distal end of the piston rod 26. Regardless of the size of the remaining axial clearance between adjusting member 20 and the distal end of the piston rod 26 (which may vary from embodiment to embodiment), a subsequent distally directed axial movement of the piston rod 26, which now effectively comprises the piston rod 26 and the adjusting member 20, is directly and unalterably transferred to the piston 18.

Thus, a drug delivery device is provided for eliminating clearance between a piston rod and a proximal end face of a piston, where the unwanted clearance can be eliminated during the manufacture or assembly of the drug delivery device (e.g., when the piston rod is inserted and mounted inside the housing component 12). Accordingly, a priming procedure by the end-user becomes superfluous.

Figure 4:
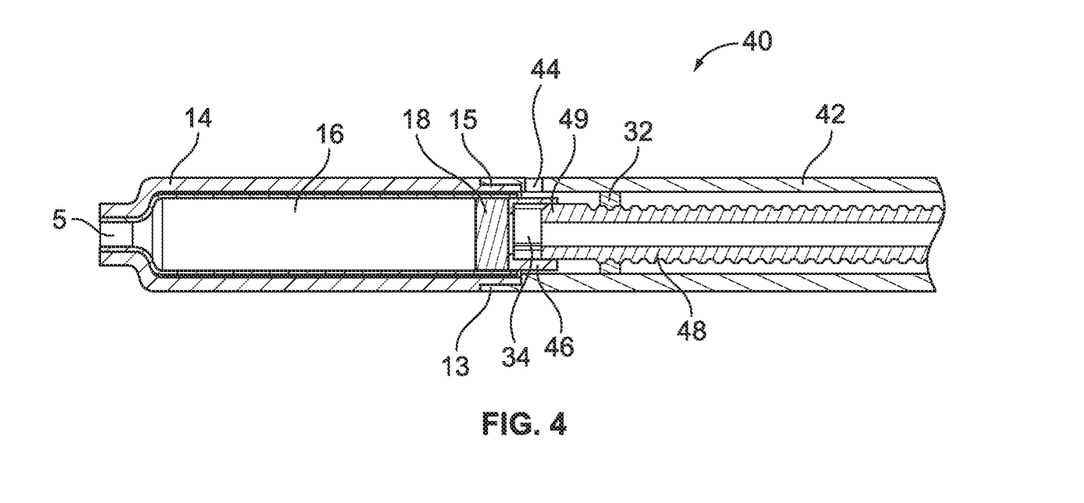
FIG. 4 illustrates a cross-sectional view of a drug delivery device, in accordance with another exemplary embodiment.
Figure 5:
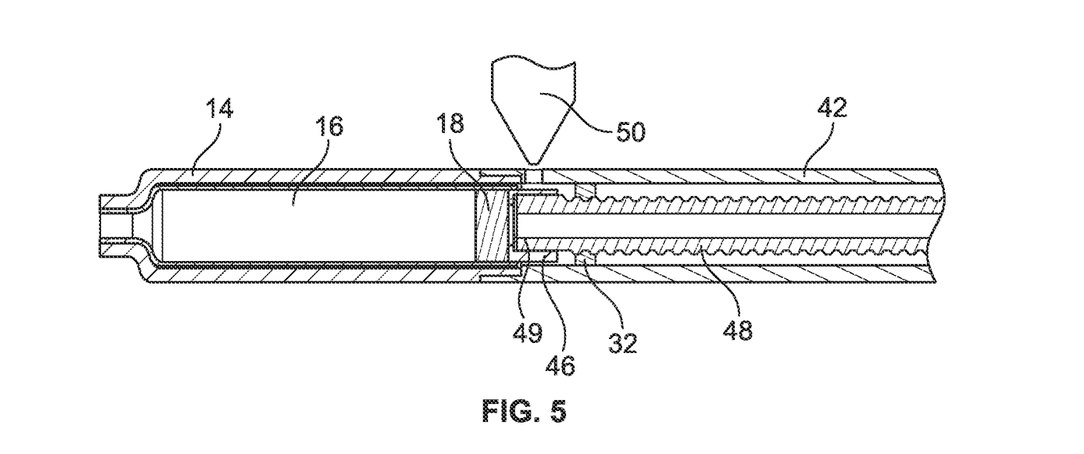
FIG. 5 illustrates the embodiment according to FIG. 4 during securement of the piston rod via externally supplied energy or adhesive.

In the embodiment according to FIGS. 4 and 5, the securing mechanism of adjusting member 46 and piston rod 48 varies from the embodiments as illustrated and described with respect to FIGS. 1-3. In addition to, or instead of, a press fit connection or any one of the above-mentioned connection/securing mechanisms, the proximal housing component 42 comprises a through opening or a transparent window 44 for the delivery of an adhesive or for the purpose of energy deposition. As in the embodiment according to FIGS. 1-3, adjusting member 46 comprises a receptacle adapted to receive a distal portion 49 of the piston rod 48. A lock rod (not shown) may be inserted into the piston rod 48 to axially move the piston rod 48 into the receptacle of the adjusting member 46 so that the piston rod 48 may be secured to the adjusting member 46. However, in other embodiments a lock rod need not be used.

Once the relative axial positions of the adjusting member 46 and piston rod 48 are such that after final assembly the adjusting member 46 abuts the proximal end face of the piston 18, as illustrated in FIG. 5, the adjusting member 46 and the piston rod 48 or an interlock member of the piston rod 48, are mutually secured by means of energy deposition, provided by, for example, a radiation source 50, such as a laser. In this way, by deposition of thermal energy in an overlapping region of adjusting member 46 and piston rod 48 or an interlock member of the piston rod 48, a direct welding of adjusting member 46 and piston rod 48 or the interlock member can be achieved. In the embodiment shown in FIGS. 4 and 5, an interlock member is not shown. However, in other embodiments, an interlock member such as the one shown in FIGS. 1-3 or the one shown in FIGS. 6 and 7 may be used.

Additionally or alternatively, it is conceivable that an adhesive or some other fixing means is externally supplied by means of the through opening 44 for locking in position adjusting member 46 and piston rod 48 or interlock member. The drug delivery device 40 according to the embodiment of FIGS. 4 and 5 may be adapted for single-use drug delivery devices, since adjusting member 46 and piston rod 48 are inseparably connected by means of welding or bonding.

Turning to FIGS. 6 and 7, two possible embodiments of drug delivery device are shown, where each uses a ratchet type connection between the adjusting member 20 or foot member and interlock member 22 of the piston rod 26. FIG. 6 illustrates a configuration where the adjusting member is attached to the proximal face 63 of piston 18 prior to assembly of the device and the interlock member 22 is attached to the distal end of the piston rod 26. As cartridge holder 14 is brought together with housing 12, the teeth, gears, or wings 60 of adjusting member 20 interface and engage with corresponding teeth 61 or recesses (between the teeth) on interlock member 22 until the respective housing are in abutment. Interlocking rod 24 is inserted into bore 62 of piston rod 26 and ultimately pushed distally into interlock member 22. This causes the interlock member to expand radially and to exert a locking force on teeth 60 and 61 forming a compression or press fit. This locking force is sufficient to prevent further axial movement of the interlock member of the piston rod into the adjusting member during dose delivery. During dose delivery, a distal movement of the piston rod 26 results in an equal movement of the adjusting member 20 and the lock rod 24.

The embodiment in FIG. 7 differs from that in FIG. 7 in that the adjusting member 20 is preassembled to interlock member 22 before cartridge holder 14 is connected to housing 12. As cartridge holder 14 is moved into position to abut housing 12, the proximal face 63 of piston 18 comes into contact with distal face 64 of adjusting member 20. This causes adjusting member 20 to move in the proximal direction, thus engaging more teeth 60 and 61, until the two housings are in abutment. At this point interlocking rod 24 is pushed in the distal direction and into interlock member 22 to secure or lock the relative axial positions of the adjusting and interlock members ensuring that the distal face 64 of adjusting member 20 is abutting proximal face 63 of the piston 18.

Although not explicitly shown in FIGS. 6 and 7, bore 62 may comprise a beveled surface at its distal end (i.e., within the interlock member 22) as shown in FIGS. 1-3. Accordingly, the beveled surface of interlock member 22 may engage the beveled surface of lock rod 24 causing the interlock member 22 to move radially outward, thus generating a press fit with the adjusting member 20.

The term "medicament," as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compounds. In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

The pharmaceutically active compound may comprise at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2, H-(Lys)5-des Pro36, des Pro37 Exendin-4(1-39)-NH2, des Pro36 [Asp28] Exendin-4(1-39), des Pro36 [IsoAsp28] Exendin-4(1-39), des Pro36 [Met(O)14, Asp28] Exendin-4 (1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met (O)14 Trp(O2)25, Asp28] Exendin-4(1-39), des Pro36 [Met (O)14 Trp(O2)25, IsoAsp28] Exendin-4(1-39); or des Pro36 [Asp28] Exendin-4(1-39), des Pro36 [IsoAsp28] Exendin-4 (1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2) 25, IsoAsp28] Exendin-4(1-39), des Pro36 [Met(O)14 Trp (O2)25, Asp28] Exendin-4(1-39), des Pro36 [Met(O)14 Trp (O2)25, IsoAsp28] Exendin-4(1-39), wherein the group -Lys6-NH2 may be bound to the C-terminus of the Exendin-4 derivative; or an Exendin-4 derivative of the sequence H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4 (1-39)-NH2, des Pro36, Pro37, Pro38 [Asp28] Exendin-4 (1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O) 14, Asp28] Exendin-4(1-39)-Lys6-NH2, des Met(O)14 Asp28 Pro36, Pro37, Pro38 Exendin-4(1-39)-NH2, H-(Lys) 6-desPro36, Pro37, Pro38 [Met(O)14, Asp28] Exendin-4(1-39)-NH2, H-Asn-(Glu)5-des Pro36, Pro37, Pro38 [Met(O) 14, Asp28] Exendin-4(1-39)-NH2, des Pro36, Pro37, Pro38 [Met(O)14, Asp28] Exendin-4(1-39)-(Lys)6-NH2, H-(Lys) 6-des Pro36, Pro37, Pro38 [Met(O)14, Asp28] Exendin-4 (1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp (O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2; or a pharmaceutically acceptable salt or solvate of any one of the aforementioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Exemplary embodiments of the present invention have been described. Those skilled in the art will understand, however, that changes and modifications may be made to these embodiments, and that the various features of these embodiments may be combined without departing from the true scope and spirit of the present invention, which is defined by the claims.

The invention claimed is:

1. A drug delivery device for dispensing medicament, comprising:
   a medicament cartridge, wherein the medicament cartridge comprises: (i) a distal end, (ii) a proximal end that is opposite the distal end along a body axis of the medicament cartridge, and (iii) a movable piston having a proximal face and being positioned substantially at the proximal end of the medicament cartridge;
   a hollow piston rod having an open distal end and an open proximal end and having an axial bore extending between the open distal and proximal ends, wherein the hollow piston rod is configured to move distally during dose delivery;
   a lock rod movably positioned within the axial bore of the hollow piston rod and having a distal portion that is capable of extending beyond the open distal end;
   an adjusting member positioned adjacent the proximal face of the movable piston and defining a receptacle along the body axis of the medicament cartridge; and
   an interlock member disposed within the receptacle of the adjusting member, wherein the interlock member is positioned at the open distal end of the hollow piston rod, and wherein the interlock member has a wall that contacts the adjusting member to form a radial press fit with the adjusting member within the receptacle when the lock rod is inserted into the axial bore of the hollow piston rod and advanced distally through the axial bore,
   wherein an axial position of the interlock member relative to the receptacle is variable and wherein the radial press fit between the wall of the interlock member and the receptacle of the adjusting member can be formed in at least two different axial positions of the interlock member relative to the receptacle,
   wherein the proximal face of the movable piston causes the adjusting member to move proximally relative to the interlock member during assembly of the drug delivery device,
   wherein the open proximal end of the hollow piston rod allows access to the lock rod so that the lock rod can be moved axially and distally during assembly of the drug delivery device to lock the interlock member with the adjusting member when a distal face of the adjusting member abuts and contacts the proximal face of the piston in a manner such that the lock rod does not connect to any portion of the piston,
   wherein during the dose delivery, a distal movement of the hollow piston rod results in an equal movement of the adjusting member and the lock rod, and
   wherein no part of the hollow piston rod contacts the movable piston.

2. The drug delivery device of claim 1, wherein the lock rod is configured for insertion into the axial bore of the hollow piston rod to fix the interlock member to the adjusting member.

3. The drug delivery device of claim 1, wherein the interlock member interacts with the adjusting member for mutually locking, securing, or fixing the hollow piston rod to the adjusting member.

4. The drug delivery device of claim 3, wherein the interlock member is located between the lock rod and the adjusting member.

5. The drug delivery device of claim 3, wherein the interlock member is coupled to the adjusting member through engagement of teeth.

6. The drug delivery device of claim 3, wherein the lock rod has a beveled distal end surface configured to engage a complementary beveled surface on the interlock member such that as the lock rod moves distally, an engagement of the beveled surfaces causes the interlock member to move radially outward to generate the radial press fit with the adjusting member.

7. The drug delivery device of claim 1, wherein the interlock member is configured such that the lock rod cannot move distally past a distal end of the interlock member, and wherein a position of the interlock member within the receptacle of the adjusting member defines an axial clearance between the adjusting member and the interlock member.

8. The drug delivery device of claim 1, wherein the interlock member is operable to lock, in position, the open distal end of the hollow piston rod with the receptacle of the adjusting member to form a mechanical coupling that is rigid in compression of the piston rod and the piston.

9. The drug delivery device of claim 1, wherein the receptacle of the adjusting member comprises a receptacle sidewall, and wherein the wall of the interlock member is operable to contact the receptacle sidewall and to form the radial press fit with the receptacle sidewall.

* * * * *

UNITED STATES PATENT AND TRADEMARK OFFICE
CERTIFICATE OF CORRECTION

PATENT NO.        : 10,549,045 B2
APPLICATION NO.   : 14/054913
DATED             : February 4, 2020
INVENTOR(S)       : Axel Forstreuter

Page 1 of 1

It is certified that error appears in the above-identified patent and that said Letters Patent is hereby corrected as shown below:

In the Specification

Column 1, Line 7, delete "divisional" and insert -- continuation --.

Signed and Sealed this
Fifth Day of May, 2020

Andrei Iancu
*Director of the United States Patent and Trademark Office*